(12) United States Patent
Sunaga et al.

(10) Patent No.: US 8,193,295 B2
(45) Date of Patent: Jun. 5, 2012

(54) AMIDE GROUP-CONTAINING SILOXANE AMINE COMPOUND

(75) Inventors: Tomoyasu Sunaga, Tochigi (JP); Junichi Ishii, Tochigi (JP); Etsuchi Nishikawa, Shizuoka (JP)

(73) Assignees: Sony Chemical & Information Device Corporation, Tokyo (JP); Ihara Chemical Industry Co., Ltd., Tokyo (JP)

( * ) Notice: Subject to any disclaimer, the term of this patent is extended or adjusted under 35 U.S.C. 154(b) by 34 days.

(21) Appl. No.: 12/452,957

(22) PCT Filed: Jul. 28, 2008

(86) PCT No.: PCT/JP2008/063520
§ 371 (c)(1),
(2), (4) Date: Jan. 29, 2010

(87) PCT Pub. No.: WO2009/025151
PCT Pub. Date: Feb. 26, 2009

(65) Prior Publication Data
US 2010/0137547 A1    Jun. 3, 2010

(30) Foreign Application Priority Data
Aug. 22, 2007 (JP) ................................. 2007-216215

(51) Int. Cl.
*C08G 77/455* (2006.01)
(52) U.S. Cl. ................................. 528/38; 528/26; 528/28
(58) Field of Classification Search ........................ None
See application file for complete search history.

(56) References Cited

U.S. PATENT DOCUMENTS

| | | | |
|---|---|---|---|
| 3,488,371 A | 1/1970 | Klebe | |
| 4,395,527 A * | 7/1983 | Berger | 528/26 |
| 4,480,009 A | 10/1984 | Berger | |
| 5,237,034 A | 8/1993 | Im et al. | |
| 5,527,862 A * | 6/1996 | Itoh et al. | 525/393 |

FOREIGN PATENT DOCUMENTS

| | | |
|---|---|---|
| JP | A-57-123223 | 7/1982 |
| JP | A-61-293224 | 12/1986 |
| JP | A-63-84188 | 4/1988 |
| JP | A-04-325523 | 11/1992 |
| JP | A-5-43700 | 2/1993 |
| JP | A-6-206856 | 7/1994 |
| JP | A-2000-173345 | 6/2000 |
| JP | A-2002-201279 | 7/2002 |
| JP | A-2003-131371 | 5/2003 |

OTHER PUBLICATIONS

Takeuchi et al., "Siloxane-Modified Polyamideimide with Excellent Adhesion and Heat-Performance," Hitachi Chemical Technical Report, No. 39, Jul. 2002, p. 29 (with Abstract and partial English translation).
Catalytic Hydrogenation, Organic Chemistry, Ed. Stanley H. Pine, 5th Ed., Dec. 2005, pp. 283, 642.
International Search Report issued in International Patent Application No. PCT/JP2008/063520 on Sep. 9, 2008.
Written Opinion of the International Search Authority issued in International Patent Application No. PCT/JP2008/063520 on Mar. 4, 2010 (with English translation).

* cited by examiner

*Primary Examiner* — Marc Zimmer
(74) *Attorney, Agent, or Firm* — Oliff & Berridge, PLC

(57) ABSTRACT

A novel amide group-containing siloxane amine compound, which is useful as a diamine component of a polybenzimidazole resin, a polybenzoxazole resin, and particularly a polyimide resin, which is derived from an amine monomer, has a chemical structure represented by the formula (1).

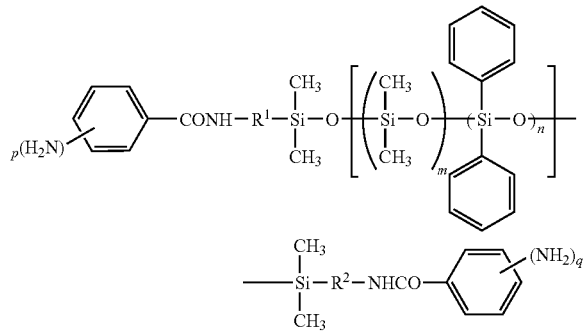

In the formula (1), $R^1$ and $R^2$ each independently represent an optionally substituted alkylene group; p denotes an integer of 0 to 3; q denotes an integer of 0 to 3; m denotes an integer of 1 to 30; and n denotes an integer of 0 to 20; provided that p and q are not 0 at the same time.

4 Claims, No Drawings

AMIDE GROUP-CONTAINING SILOXANE AMINE COMPOUND

TECHNICAL FIELD

The present invention relates to a novel amide group-containing siloxane amine compound.

BACKGROUND ART

When producing a flexible printed wiring board or rigid wiring board, a liquid resist or a dry film composed of a resin composition on a copper clad laminate as a base, and a polyimide film provided with an adhesive are commonly used as a cover material. Furthermore, a photosensitive resin composition (liquid photosensitive resist) and a photosensitive dry film to which a photosensitive property is imparted are also used as a photosensitive cover film. Examples of the constituent materials of these include polybenzimidazole resins, polybenzoxazole resins, and polyimide resins which have excellent heat resistance. However, in terms of ease of resin production and production cost, polyimide resins particularly are very useful.

Such flexible printed wiring boards and rigid wiring boards have a laminate structure of organic and inorganic materials. Depending on the materials constituting the laminate, warping of the substrate can occur. Warping can be expressed by the following formula based on the physical properties of the respective constituent materials. Therefore, while there are several approaches, considering the case of a polyimide type cover material, these wiring boards can be prevented from warping by reducing the elastic modulus of the film itself which is composed of the polyimide resin. To cope with such a demand, it has been proposed to use a siloxane diamine as one of the plurality of diamine components constituting the polyimide resin (Patent Document 1). Furthermore, it is also required to improve the film-forming properties and chemical resistance of a polyimide resin which uses such a siloxane diamine. To meet these demands, a vinyl ether residue is introduced into the polyimide resin as a crosslinking group capable of reacting with the acrylate.

$$(\text{Warping}) = \int_{T_{cure}}^{T_0} \frac{E_f}{1-v_f}(\alpha_f - \alpha_s) dT$$

$T_{cure}$: Temperature applied on the laminate
$E_f$: Elasticity of material
$\alpha_f$: Coefficient of thermal expansion of material
$\alpha_s$: Coefficient of thermal expansion of substrate
$v_f$: Constant
[Patent Document 1] Japanese Patent Application Laid-Open No. 2003-131371

DISCLOSURE OF THE INVENTION

Problems to be Solved by the Invention

However, although the intended low elastic modulus can be imparted to a film formed from a polyimide resin prepared using a siloxane diamine like that described in Patent Document 1, there is the problem that electroless Ni/Au plating resistance deteriorates. Furthermore, the vinyl ether residue is introduced into a polyimide resin isolated from a polyimide-containing resultant obtained by reacting siloxane diamine with acid dianhydride. Therefore, this cannot be said to be an advantageous introduction method in terms of industrial productivity.

The present invention is directed to solving the above-described problems in the conventional art. It is an object of the present invention to enable a film formed from a polybenzimidazole resin, a polybenzoxazole resin, and particularly a polyimide resin, to be provided with a comparatively low elastic modulus and good electroless plating resistance. Furthermore, it is also an object of the present invention to enable a group having a hydrogen bond forming ability or a crosslink forming ability (crosslinking point) to be introduced into a polyimide resin in advance.

Means for Solving the Problems

The present inventor found that the above-described objects can be achieved by using a novel amide group-containing siloxane amine compound with a specific structure having amide groups in its molecule as a siloxane diamine constituting a polybenzimidazole resin, a polybenzoxazole resin, or a polyimide resin, thereby completing the present invention.

More specifically, the present invention provides a novel amide group-containing siloxane amine compound represented by the following formula (1).

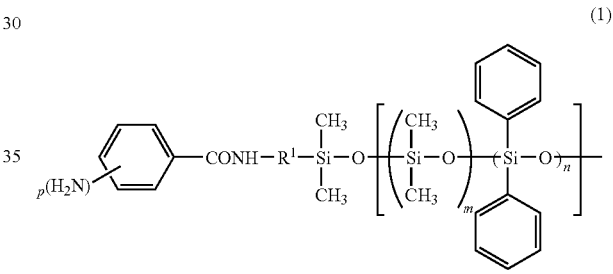

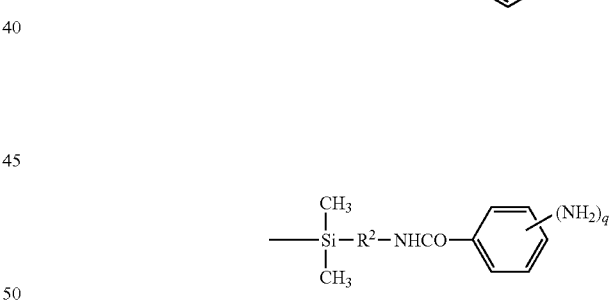

In the formula (1), $R^1$ and $R^2$ each independently represent an alkylene group which may be substituted; p denotes an integer o' f 0 to 3; q denotes an integer of 0 to 3; m denotes an integer of 1 to 30; and n denotes an integer of 0 to 20; provided that p and q are not 0 at the same time.

Furthermore, the present invention provides a method for producing the amide group-containing siloxane amine compound represented by the formula (1), the method including reacting nitrobenzoyl halides represented by the formula (3) and the formula (3') with a siloxane diamine compound represented by the formula (2) to form an amide group-containing siloxane nitro compound represented by the formula (4), and reducing the nitro groups thereof to obtain the amide group-containing siloxane amine compound represented by the formula (1), as illustrated by the following reaction scheme A.

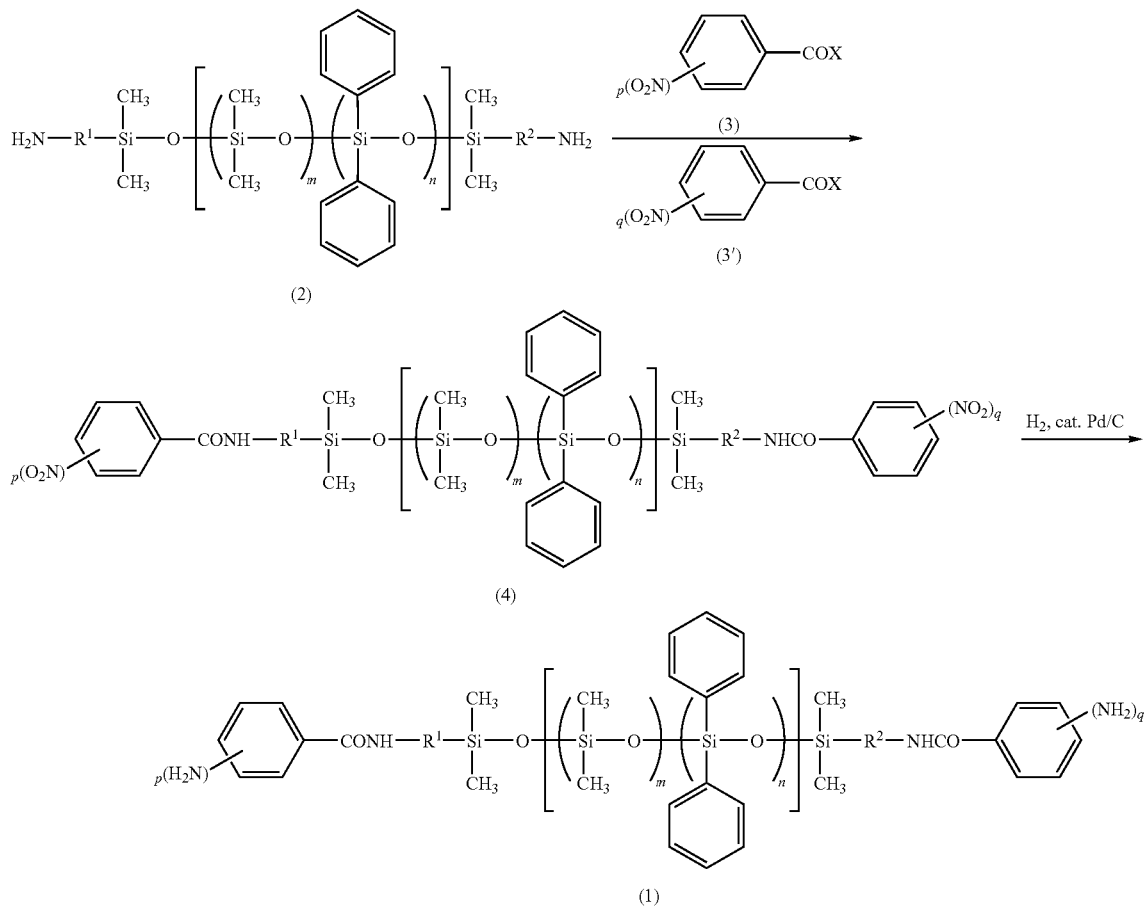

In the formulae (1) to (4), $R^1$, $R^2$, p, q, m, and n are as already described for the formula (1), and X represents a halogen atom such as fluorine, chlorine, bromine, and iodine.

ADVANTAGES OF THE INVENTION

The novel amide group-containing siloxane amine compound according to the present invention has a siloxane unit. Therefore, the elastic modulus of a polybenzimidazole resin, a polybenzoxazole resin, and particularly a polyimide resin, can be reduced. Furthermore, because the amide group-containing siloxane amine compound of the present invention has an amide bond in the molecule, the adhesion between the polyimide resin and a conduction part, such as the copper on a wiring board, can be improved. In addition, since the amide group functions as a crosslinking group by an addition reaction or insertion reaction with an epoxy group, an operation for introducing a crosslinking group after isolating the polyimide resin is unnecessary.

BEST MODE FOR CARRYING OUT THE INVENTION

The novel amide group-containing siloxane amine compound according to the present invention has a chemical structure represented by the formula (1).

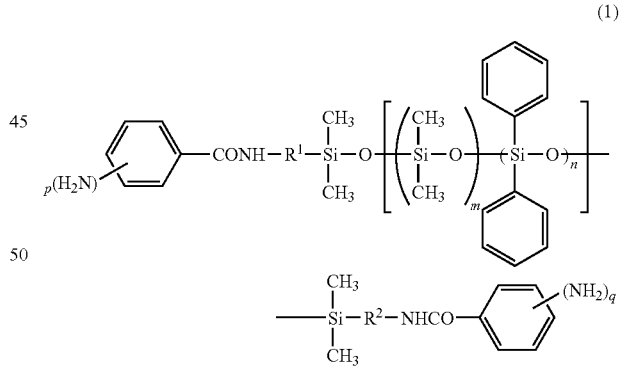

(1)

In the formula (1), the alkylene group, which may be substituted, of $R^1$ and $R^2$ is preferably an alkylene group having 1 to 12 carbon atoms, and more preferably an alkylene group having 2 to 6 carbon atoms. Specific examples thereof include a methylene group, an ethylene group, a trimethylene group, a tetramethylene group, a pentamethylene group, and a hexamethylene group. Examples of a substituent of this alkylene group include a linear- or branched-chain alkyl group having 1 to 8 carbon atoms such as a methyl group or an ethyl group, and a monocyclic or fused ring aryl group having 1 to 14 carbon atoms such as a phenyl group. Among these, from the perspective of reactivity with the nitrobenzoyl halide, a trimethylene group is particularly preferred as $R^1$ and $R^2$. Furthermore, while $R^1$ and $R^2$ may be the same or different, it is preferred that $R^1$ and $R^2$ are the same, as this avoids difficulty in obtaining the raw materials.

Furthermore, although m denotes an integer of 1 to 30, m is preferably an integer of 1 to 20, and more preferably an integer of 2 to 20. This is because if m is 0, it is difficult to obtain the raw materials, while if m is more than 30, the compound does not mix in the reaction solvent and remains separated. On the other hand, although n denotes an integer of 0 to 20, n is preferably an integer of 1 to 20, and more preferably an integer of 1 to 10. This is because if n is 1 or more, a diphenyl siloxane unit having excellent flame retardance is introduced, so that the resultant compound has better heat resistance than when such a unit is not introduced. In addition, if n is more than 20, the contribution to a lower elasticity is reduced.

While p and q denote integers of 0 to 3, and are not 0 at the same time, it is preferred that p and q are 1. As an embodiment of the amino phenyl group at the ends of its molecular structure, if p or q is 1, when the carbon atom of the phenyl group bonded to the carbonyl carbon is designated as the 1-position, the amino group is at the 2-position, 3-position, or 4-position of the phenyl group. If p or q is 2, the amino groups are at the 2- and 4-positions, the 2- and 6-positions, the 2- and 3-positions, the 2- and 5-positions, the 3- and 4-positions, or the 3- and 5-positions of the phenyl group. If p or q is 3, the amino groups are at the 2-, 3-, and 4-positions, the 2-, 3-, and 5-positions, the 2-, 3-, and 6-positions, the 2-, 4-, and 5-positions, the 2-, 4-, and 6-positions, or the 3-, 4-, and 5-positions of the phenyl group. Of these, from the perspective of easily obtaining the raw materials, if p or q is 1, the amino group is preferably at the 4-position of the phenyl group, if p or q is 2, the amino groups are preferably at the 2- and 4-positions of the phenyl group, and if p or q is 3, the amino groups are preferably at the 2-, 4-, and 6-positions of the phenyl group.

The number of p and q of the amino group in the amino phenyl group at both ends of the novel amide group-containing siloxane amine compound may be the same or different.

Although the number average molecular weight of the novel amide group-containing siloxane amine compound according to the present invention varies depending on the number of p, q, m, and n, the number average molecular weight thereof is preferably 500 to 3,000, and more preferably 1,000 to 2,000.

The novel amide group-containing siloxane amine compound according to the present invention has an amide bond at either end of the molecule. Thus, the polyimide resin prepared from the amide group-containing siloxane amine compound will also continue to have the amide bonds. Therefore, the adhesion between a polyimide resin derived from the novel amide group-containing siloxane amine compound of the present invention and a conduction part, such as the copper on a wiring board, improves. In addition, amide groups are known to undergo an addition reaction or insertion reaction with an epoxy group (Hitachi Chemical Technical Report, No. 39 (2002-7), page 29). Therefore, if an epoxy resin commonly used in resin compositions or dry films is combined with the polyimide resin derived from the novel amide group-containing siloxane amine compound according to the present invention, the amide group functions as a crosslinking group. Consequently, an operation for introducing a crosslinking group after isolating the polyimide resin is unnecessary.

The novel amide group-containing siloxane amine compound of the present invention represented by the formula (1) can be produced according to the following scheme A.

<Reaction Scheme A>

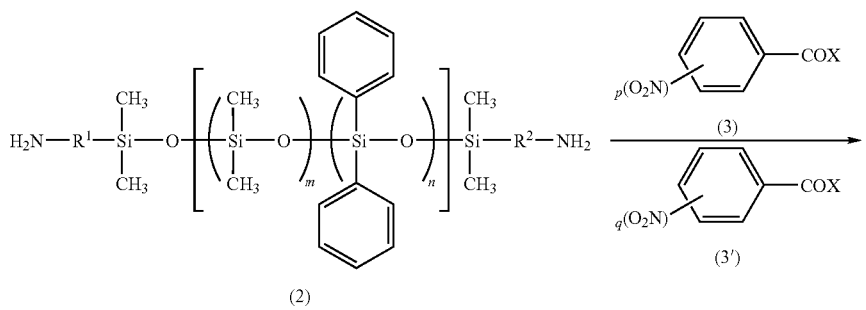

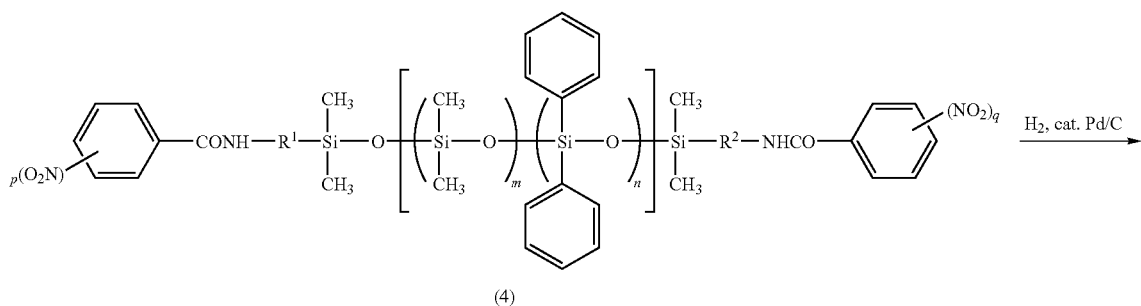

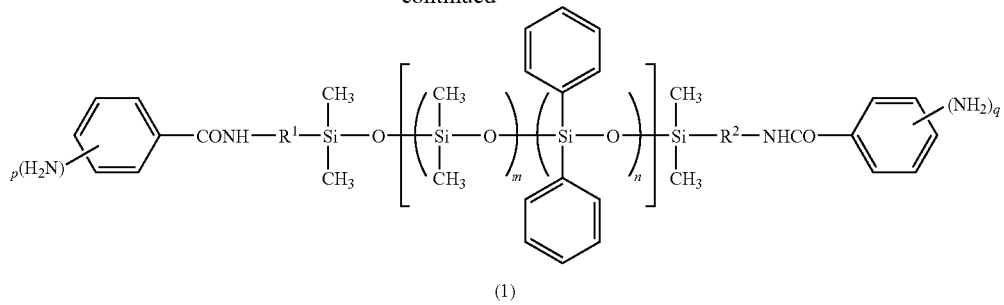

(1)

In the formulae (1) to (4), $R^1$, $R^2$, p, q, m, and n are as already described for the formula (1), and X represents a halogen atom such as fluorine, chlorine, bromine, and iodine.

In the method for producing the amide group-containing siloxane amine compound according to the present invention represented by the formula (1), first, an amide group-containing siloxane nitro compound represented by the formula (4) is formed by subjecting a siloxane diamine compound represented by the formula (2) and nitrobenzoyl halides represented by the formula (3) and the formula (3') to a nucleophilic substitution reaction in the presence of a base and a solvent.

Examples of the siloxane diamine compound represented by the formula (2) include, as a compound containing only a methyl group on a siloxane side chain, KF-8010, X-22-161A, X-22-161B, KF-8008, KF-8012 (all available from Shin-Etsu Chemical Co. Ltd.), BY16-871, BY-16-853C, BY-16-853U (all available from Dow Corning Toray Co., Ltd.), Sila-Ace FM-3311 (Chisso Corporation) and the like. Furthermore, as a compound containing a methyl group and a phenyl group on a siloxane side chain, examples of the siloxane diamine compound represented by the formula (2) include X-22-9409, X-22-1660B-3 (both available from Shin-Etsu Chemical Co. Ltd.) and the like.

Examples of the nitrobenzoyl halides compound represented by the formula (3) and the formula (3') include: mono-nitrobenzoyl halides such as 2-nitrobenzoyl chloride, 3-nitrobenzoyl chloride, 4-nitrobenzoyl chloride, 2-nitrobenzoyl bromide, 3-nitrobenzoyl bromide, 4-nitrobenzoyl bromide, 2-nitrobenzoyl iodide, 3-nitrobenzoyl iodide, 4-nitrobenzoyl iodide, 2-nitrobenzoyl fluoride, 3-nitrobenzoyl fluoride, and 4-nitrobenzoyl fluoride; dinitrobenzoyl halides such as 2,3-dinitrobenzoyl chloride, 2,4-dinitrobenzoyl chloride, 2,5-dinitrobenzoyl chloride, 2,6-dinitrobenzoyl chloride, 3,4-dinitrobenzoyl chloride, 3,5-dinitrobenzoyl chloride, 4,5-dinitrobenzoyl chloride, and the corresponding bromides, fluorides, and iodides; and trinitrobenzoyl halides such as 2,3,4-trinitrobenzoyl chloride, 2,3,5-trinitrobenzoyl chloride, 2,3,6-trinitrobenzoyl chloride, 2,4,5-trinitrobenzoyl chloride, 2,4,6-trinitrobenzoyl chloride, 3,4,5-trinitrobenzoyl chloride, 3,4,6-trinitrobenzoyl chloride, and the corresponding bromides, fluorides, and iodides.

The molar ratio of the diamine and the nitrobenzoyl halide can be represented by ([siloxane diamine compound represented by the formula (2)]/[nitrobenzoyl halide represented by the formula (3)]+[nitrobenzoyl halide represented by the formula (3')]). The molar ratio of the diamine and the nitrobenzoyl halide is (1.0/2.0) to (1.0/10.0), preferably (1.0/2.2) to (1.0/7.0), and more preferably (1.0/2.4) to (1.0/6.0).

Examples of the base which can be used in the present step include: an alkali metal organic compound such as phenyl sodium; an alkali metal alcoholate such as sodium methylate, sodium ethylate, t-butoxy potassium, and t-butoxy sodium; an alkali metal carboxylate such as sodium acetate, potassium acetate, and sodium propionate; an inorganic base such as sodium hydroxide, potassium hydroxide, calcium hydroxide, cesium hydroxide, sodium carbonate, potassium carbonate, cesium carbonate, sodium bicarbonate, potassium bicarbonate, sodium phosphate, and sodium hydrogen phosphate; a so-called organic base as represented by a tertiary amine such as pyridine, (4-dimethylamino)pyridine (DMAP), picoline, isoquinoline, trimethylamine, triethylamine, N,N-diisopropylethylamine, diisopropylamine, 1,4-diazabicyclo[2.2.2]octane (DABCO), and 1,8-diazabicyclo[5.4.0]undecene (DBU); and the like. Of these, an organic base as represented by a tertiary amine is preferred. More preferred are pyridine, (4-dimethylamino)pyridine (DMAP), trimethylamine, triethylamine, N,N-diisopropylethylamine, and diisopropylamine. Still more preferred are triethylamine, N,N-diisopropylethylamine, and diisopropylamine. Particularly preferred is triethylamine.

The molar ratio of the diamine and the base can be represented by ([siloxane diamine compound represented by the formula (2)]/[base]). The molar ratio of the diamine and the base is (1.0/2.0) to (1.0/10.0), preferably (1.0/2.2) to (1.0/7.0), and more preferably (1.0/2.4) to (1.0/6.0).

As the solvent which can be used in the present step, any solvent may be used as long as it does not hinder the reaction and is stable. Examples thereof include: ethers such as phenyl ether, anisole, 1,2-dimethoxyethane, 1,2-diethoxyethane, tetrahydrofuran, and 1,4-dioxane; aromatic hydrocarbons such as toluene, xylene, mesitylene, and tetralin; alicyclic hydrocarbons such as decalin; aprotic polar solvents such as N,N-dimethylformamide, N,N-dimethylacetamide, N,N-dimethylimidazolidinone, N-methylpyrrolidone, dimethylsulfoxide, and sulfolane; aromatic nitro compounds such as nitrobenzene and p-nitrotoluene; aromatic halides such as chlorobenzene, o-dicyclobenzene, and trichlorobenzene; and the like. Preferred are aromatic hydrocarbons such as toluene, xylene, mesitylene, and tetralin, and more preferred is toluene. The solvent may be used alone, or as a mixed solvent having an arbitrary ratio.

The reaction temperature in the present step is usually in the range of −20 to 180° C., preferably 10 to 150° C., and more preferably 30 to 130° C. While a definitive reaction time cannot be stated, as this depends on the used materials, the reaction scale, the molar ratios, and the reaction temperature, the reaction time is usually from 0.1 to 24 hours, and preferably from 0.5 to 10 hours.

Concerning the production of the amide group-containing siloxane nitro compound represented by the formula (4), reference may also be made to Organic Chemistry, Fifth Edition, page 283 (Ed. Stanley H. Pine).

Next, the nitro groups of the amide group-containing siloxane nitro compound represented by the formula (4) are reduced to amino groups, whereby the novel amide group-containing siloxane amine compound represented by the formula (1) is obtained. The reduction method is not particularly limited, as long as the compound represented by the formula (1) can be obtained by converting the nitro groups into the amino groups. Examples of the reduction method may include contacting the amide group-containing siloxane nitro compound represented by the formula (4) with excess hydrogen in the presence of a precious metal catalyst, represented by a palladium-carbon catalyst, a Raney nickel catalyst and the like, in a mixed solvent of ethyl acetate and ethanol (Catalytic Hydrogenation, Organic Chemistry, Fifth Edition, page 642 (Ed. Stanley H. Pine), and reducing the nitro groups to the amino groups by so-called iron powder reduction, in which a reaction is carried out using an excess hydrogen source, such as acetic acid in the amount of the solvent, and iron.

The obtained novel amide group-containing siloxane amine compound can be formed into a polyimide resin which already includes an amide group that functions as a crosslinking agent for an epoxy resin by reacting the obtained amide group-containing siloxane amine compound with an acid dianhydride such as 3,3',4,4'-diphenylsulfone tetracarboxylic dianhydride (DSDA) to form a polyimide. In this case, the polyimide may also be formed by using with another diamine, such as 3,3'-diamino-4,4'-dihydroxydiphenylsulfone (BSDA). A resin composition or dry film formed from the obtained polyimide resin exhibits a comparatively low elastic modulus and good plating resistance.

EXAMPLES

The present invention will now be described in more detail with the following examples.

Example 1

A 2 L (liter) reaction vessel equipped with a cooling device, a thermometer, a dropping funnel, and a stirring device was, as described in the following reaction scheme B, charged with 500 g of toluene, 200 g (0.148 mol) of siloxane diamine (2a) (X-22-9409: Shin-Etsu Chemical Co. Ltd.), and 30 g (0.297 mol) of triethylamine. Then, a solution produced by dissolving 54.7 g (0.295 mol) of 4-nitrobenzoyl chloride in 300 g of toluene was added into the dropping funnel. While stirring the contents of the reaction vessel, the temperature was increased to 50° C., and then the solution in the dropping funnel was added dropwise over 1 hour. After the dropping was finished, the temperature was increased, and the mixture was stirred for 6 hours while heating to reflux. After the reaction finished, the reaction mixture was cooled to 30° C. The mixture was then charged with 800 g of water and strongly stirred. The mixture was transferred to a separatory funnel, and left to stand to separate. The thus-separated mixture was washed three times with 300 g of a 5% aqueous sodium hydroxide solution, and then washed twice with 300 g of a saturated aqueous sodium chloride solution. The organic layer was dried over magnesium sulfate, and concentrated by removing the toluene solvent by heating under reduced pressure. The resultant product was dried at 60° C. under reduced pressure for 1 day to obtain α-(p-nitrobenzoyliminopropyldimethylsiloxy)-ω-(p-nitrobenzoyliminopropyldimethylsilyl)oligo(dimethylsiloxane-co-diphenylsiloxane) (hereinafter, dinitro product (4a)) in a yield of 235 g (96% yield). The dinitro product (4a) was a pale yellow oil.

112 g (0.068 mol) of the obtained dinitro product (4a) was charged into a 1 L reaction vessel equipped with a stirrer, a hydrogen feed pipe, and a hydrogen-filled ball, along with 180 g of ethyl acetate, 320 g of ethanol, and 20 g (water content 500) of 2% palladium-carbon. The air inside the reaction vessel was purged to form a hydrogen atmosphere, and then the mixture was stirred for 2 days under an internal pressure of the hydrogen-filled ball. The catalyst was removed from the reaction mixture by filtration. The resultant reaction solution was concentrated by heating under reduced pressure, and then dried under reduced pressure at 60° C. for 2 days, whereby α-(p-aminobenzoyliminopropyldimethylsiloxy)-ω-(p-aminobenzoyliminopropyldimethylsilyl) oligo(dimethylsiloxane-co-diphenylsiloxane) (diamine product (1a): the novel amide group-containing siloxane amine compound according to the present invention) was obtained as a pale yellow oil in a yield of 102 g (95% yield).

The amine value of the obtained novel diamine product (1a) was 69.96 KOH mg/g, and the amino group equivalent was 802 g/mol. The amine value was measured using an automatic potentiometric titrator (AT-550, manufactured by Kyoto Electronics & Manufacturing Co., Ltd.). The amino group equivalent was calculated based on 56.106/(amine value)×1000.

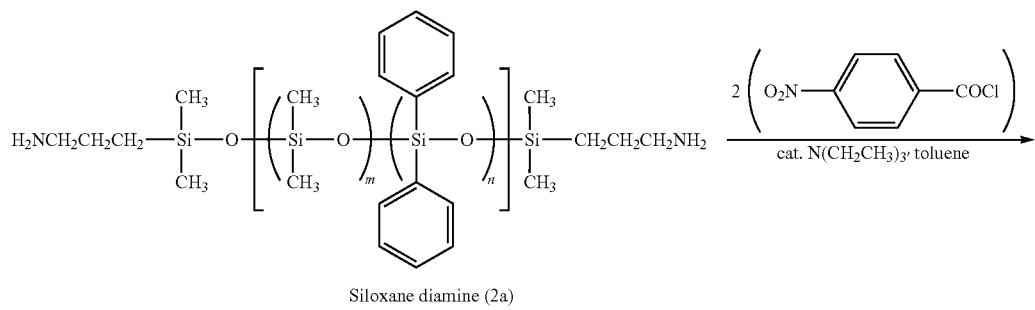

Siloxane diamine (2a)

-continued

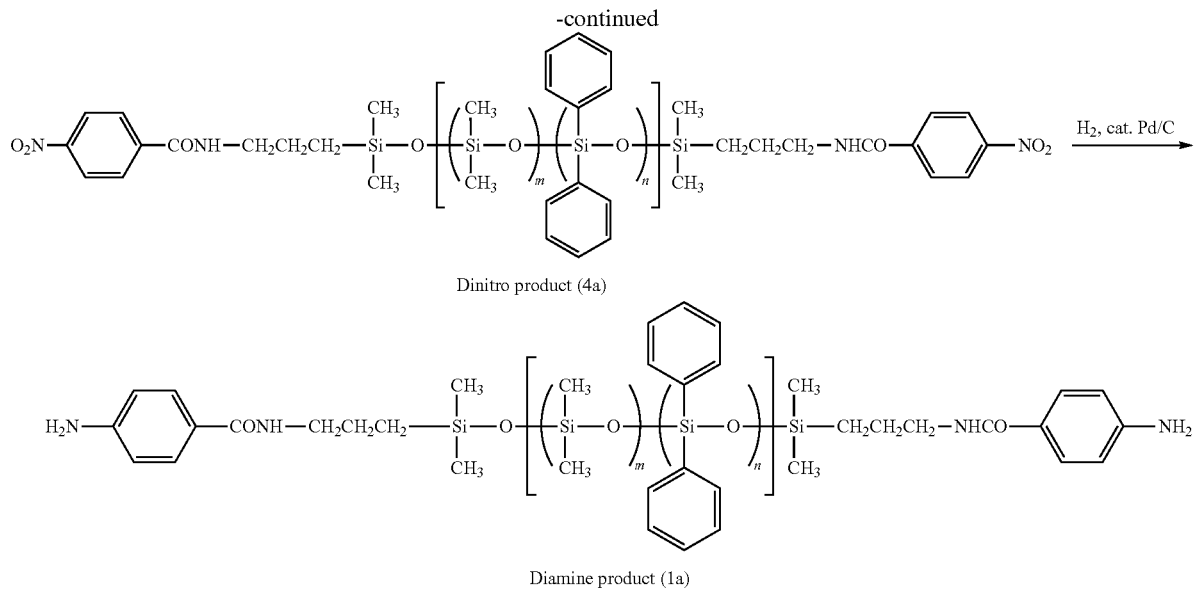

Dinitro product (4a)

Diamine product (1a)

Furthermore, the infrared spectrum and $^1$H-NMR spectrum of the diamine product (1a), which is the obtained novel amide group-containing siloxane amine compound, were measured. The results confirmed that the intended product was obtained. The infrared spectrum was measured by a transmission method using a Fourier transform infrared spectrometer (FT-IR420, Jasco Corporation). The $^1$H-NMR spectrum was measured in heavy chloroform using an NMR spectrometer (Mercury VX-300, Varian Technologies Japan Limited). These results are shown below.

IR spectrum: 3450 cm$^{-1}$ ($v_{N-H}$), 3370 cm$^{-1}$ ($v_{N-H}$), 3340 cm$^{-1}$ ($v_{N-H}$), 3222 cm$^{-1}$ ($v_{N-H}$), 1623 cm$^{-1}$ ($v_{C=O}$), 1260 cm$^{-1}$ ($v_{CH_3}$), 1000-1100 cm$^{-1}$ ($v_{Si-O}$)

$^1$H-NMR (CDCl$_3$, δ): −0.2-0.2 (m, methyl), 0.4-0.6 (m, 4H, methylene), 1.4-1.8 (m, 4H, methylene), 3.2-3.5 (m, 4H, methylene), 3.9 (bs, 4H, hydrogen atoms of amino group), 5.8-6.3 (m, 2H, hydrogen atoms of amide group), 6.4 (m, 4H, aromatic hydrogen atoms adjacent to amino group), 7.1-7.7 (m, aromatic hydrogen atoms)

Example 2

A 1 L reaction vessel equipped with a cooling device, a thermometer, a dropping funnel, and a stirring device was, as described in the following reaction scheme C, charged with 250 g of toluene, 100 g (0.219 mol) of dimethylsiloxane diamine (2b), and 23 g (0.228 mol) of triethylamine. Then, using a solution produced by dissolving 42 g (0.226 mol) of 4-nitrobenzoyl chloride in 150 g of toluene, the same operation as in Example 1 was carried out to obtain 128 g (97% yield) of α-(p-nitrobenzoyliminopropyldimethylsiloxy)-ω-(p-nitrobenzoyliminopropyldimethylsilyl)oligodimethylsiloxane (hereinafter, dinitro product (4b)) as a pale yellow oil.

128 g (0.106 mol) of the dinitro product (4b) synthesized by the above operation was charged into a 1 L reaction vessel equipped with a stirrer, a hydrogen feed pipe, and a hydrogen sphere, along with 180 g of ethyl acetate, 320 g of ethanol, and 20 g (water content 50%) of 2% palladium-carbon. Hydrogenation reduction was then carried out by performing the same operation as in Example 1, to obtain 118 g (97% yield) of α-(p-aminobenzoyliminopropyldimethylsiloxy)-ω-(p-aminobenzoyliminopropyldimethylsilyl)oligodimethylsiloxane (diamine product (1b): the novel amide group-containing siloxane amine compound according to the present invention) as a pale yellow oil.

The amine value of the obtained diamine product (1b) was 96.6 KOH mg/g, and the amino group equivalent was 581 g/mol.

<Reaction Scheme C>

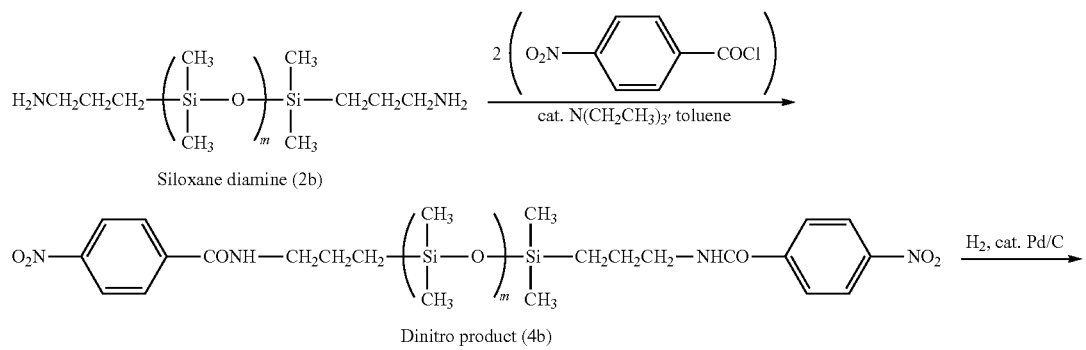

Siloxane diamine (2b)

Dinitro product (4b)

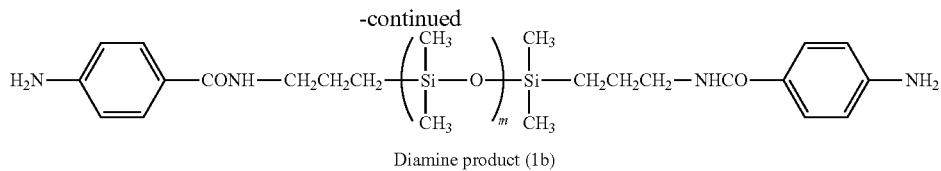

Diamine product (1b)

Reference Example 1

A 20 L reaction vessel equipped with a nitrogen feed pipe, a stirring device, and a Dean-Stark trap was charged with a mixed solution of 4,460.6 g (3.30 mol) of a siloxane diamine compound (X-22-9409, Shin-Etsu Chemical Co. Ltd.), 1,912.7 g (5.34 mol) of 3,3',4,4'-diphenylsulfone tetracarboxylic dianhydride (DSDA, New Japan Chemical Co., Ltd., 99.70% purity), 287 g of γ-butyrolactone, and 89.0 g (54.3 mmol, 97.10% purity) of the novel amide group-containing siloxane amine compound obtained in Example 1, and with 2,870 g of triglyme. The resultant mixture was stirred, charged with a further 1,100 g of toluene, and then heated to reflux for 2 hours at 185° C. Then, dewatering was carried out under reduced pressure to prepare a solution of an acid anhydride with oligo-imide ends.

The obtained solution of an acid anhydride with oligo-imide ends was cooled to 80° C., and then charged with a dispersion of 3,431 g of triglyme, 413 g of γ-butyrolactone, and 537.80 g (1.92 mol) of 3,3'-diamino-4,4'-dihydroxydiphenylsulfone (BSDA, Konishi Chemical Ind. Co., Ltd., 99.70% purity). The resultant mixture was stirred for 2 hours at 80° C., then charged with 524 g of triglyme, and heated to reflux for 2 hours at 185° C. The mixture was cooled to room temperature, and the toluene and water which had accumulated in the trap were removed by distillation. From this operation, a novel polyimide compound having amide groups was synthesized.

To 100 parts by mass of the obtained polyimide resin were charged 10 parts by mass of diazonaphthoquinone (4NT-300, Toyo Gosei Co., Ltd.) as a photosensitizing agent, 2 parts by mass of an epoxy resin (JER 807, Japan Epoxy Resins Co., Ltd.) as a crosslinking agent, 5 parts by mass of 6,6-(1-methylidene)bis[3,4-dihydro-3-phenyl-2H-1,3-benzoxazine] (BF-BXZ, Konishi Chemical Ind. Co., Ltd.) as an oxazine compound, and 0.3 parts by mass of an anti-corrosion agent (CDA-10, ADEKA Corporation). The resultant mixture was mixed until it was uniform to prepare a polyimide resin composition (a). The obtained polyimide resin composition (a) was, as described below, subjected to test evaluations for developability, electroless Ni/Au plating resistance, curl properties, and flame retardance.

(Developability)

The polyimide resin composition (a) was coated on one side of a copper foil of about 0.3 μm which had been subjected in advance to a chemical polishing treatment so that the dry thickness would be 10 μm. A test piece A was produced by drying the coated composition for 10 minutes at 80° C. to form a polyimide resin layer on one side of the copper foil. The polyimide resin layer of the obtained test piece A was irradiated via an exposure mask having a given positive pattern with a cumulative amount of light being 2,500 mJ/cm² using an ultra high pressure mercury lamp (including three rays of the g-ray, the h-ray and the i-ray). Subsequently, the test piece A was dipped in a 3% aqueous sodium hydroxide solution heated at 40° C. and then dipped for 2 minutes in warm water heated at 40° C. to carry out alkali development. Furthermore, the test piece A was neutralized by dipping it in a 10% aqueous sulfuric acid solution, then thoroughly washed with distilled water, and dried to complete the series of development processes. If the dipping time in the 3% aqueous sodium hydroxide solution is 60 seconds or less, alkali developability can be evaluated as being at a practical level. In the present test, the development time was 60 seconds or less, and thus practical alkali developability was realized.

(Electroless Ni/Au Plating Resistance)

The test piece A used in the developability test was heated for 1 hour at 200° C. in a nitrogen atmosphere to complete crosslinking of the polyimide resin layer (post-baking). Next, an electroless nickel plating treatment (used plating solution: NPR-4) was carried out, which was followed by carrying out an electroless gold plating treatment (used plating solution: TKK-51). If the discoloration range of the polyimide resin layer around the conductor aperture of the test piece A after the electroless Ni/Au plating is less than 50 μm from the edge, the electroless Ni/Au resistant can be evaluated as being at a practical level. In the present test, the discoloration range was less than 50 μm, and thus practical electroless Ni/Au plating resistance was realized. The reason for this is that because the novel polyimide compound having amide groups obtained in Reference Example 1 was used, due to the presence of the amide group, the adhesive force between the polyimide resin layer and the copper improved.

(Curl Properties)

The polyimide resin composition (a) was coated on one side of a flat 25 μm-thick polyimide film for original fabric (Upilex 25S) so that the dry thickness would be 10 μm. A test piece B was obtained by drying the coated composition for 10 minutes at 80° C., and then heating for 1 hour at 200° C. in a nitrogen atmosphere to complete crosslinking of the polyimide resin layer (post-baking). The obtained test piece B was cut into a 10 cm-square, and placed on a flat plate so that the inner side of the curling faced the ceiling. The lift of the four corners was measured, and the average value thereof was calculated. If this average value is less than 10 mm, the curl properties can be evaluated as being at a practical level. In the present test, the calculated average value was less than 10 mm, and thus practical curl properties were realized. The reason for this is that the novel polyimide compound having amide groups obtained in Reference Example 1 has a sufficiently low elastic modulus.

(Flame Retardance)

The polyimide resin composition (a) was coated on both sides of a flat 25 μm-thick polyimide film for original fabric (Upilex 25S) so that the respective dry thicknesses would be 10 μm. A test piece C was obtained by drying the coated composition for 10 minutes at 80° C., and then heating for 1 hour at 200° C. in a nitrogen atmosphere to complete crosslinking of the polyimide resin layer (post-baking). The obtained test piece C was tested based on the UL-94-VTM standard. The test piece C satisfied the UL-94-VTM-0 standard, meaning that favorable flame retardance was realized. The reason for this is that the novel polyimide compound having amide groups obtained in Reference Example 1 has a siloxane skeleton having a high flame retardance effect.

Reference Example 2

Polyimide synthesis was carried out in the same manner as in Reference Example 1, except that 73.3 g (54.3 mmol) of a siloxane diamine compound (X-22-9409, Shin-Etsu Chemical Co. Ltd.) was used instead of the novel amide group-containing siloxane amine compound obtained in Example 1. Then, the obtained polyimide was subjected to test evaluations for developability, electroless Ni/Au plating resistance, curl properties, and flame retardance. The results showed that since the novel amide group-containing siloxane amine compound obtained in Example 1 was not used, regarding the electroless Ni/Au plating resistance, the discoloration range was 50 μm or more, and thus a practical electroless Ni/Au plating resistance could not be realized.

Industrial Applicability

The novel amide group-containing siloxane amine compound according to the present invention can reduce the elastic modulus of a polybenzimidazole resin, a polybenzoxazole resin, and particularly a polyimide resin, which are derived therefrom. Accordingly, the resulting resin can be prevented from curling. Furthermore, the amide group-containing siloxane amine compound of the present invention has an amide bond in the molecule, and can improve the adhesion between the polyimide resin and a wiring board formed from a metal wiring layer or a polyimide. In addition, since the amide group undergoes an addition reaction or insertion reaction with an epoxy group, the amide group functions as a crosslinking point. Therefore, an operation for introducing a crosslinking group after isolating the polyimide resin is unnecessary. Accordingly, the novel amide group-containing siloxane amine compound according to the present invention is useful as a diamine component of a polyimide resin for a resin composition or dry film for an electronic part.

The invention claimed is:

1. A method for producing an amide group-containing siloxane amine compound represented by the formula (1), the method comprising: reacting nitrobenzoyl halides represented by the formula (3) and the formula (3') with a siloxane diamine compound represented by the formula (2) to form an amide group-containing siloxane nitro compound represented by the formula (4); and reducing the nitro groups thereof to obtain the amide group-containing siloxane amine compound represented by the formula (1):

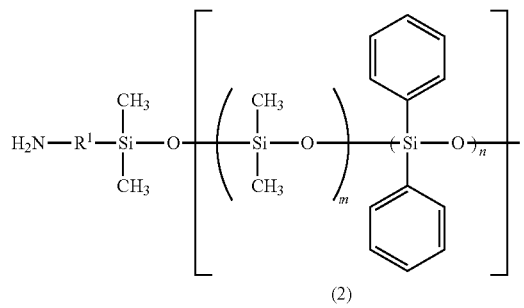

(2)

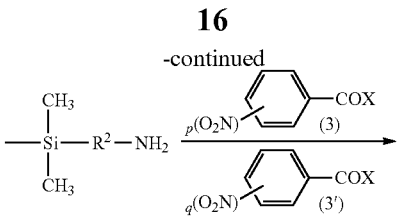

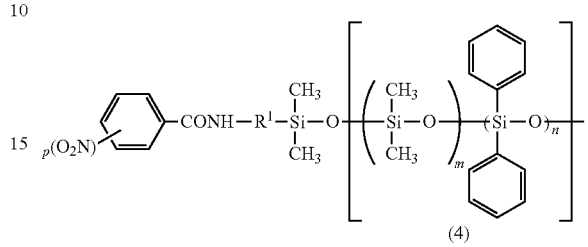

(4)

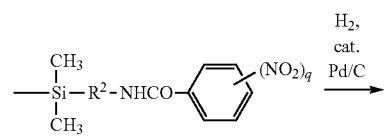

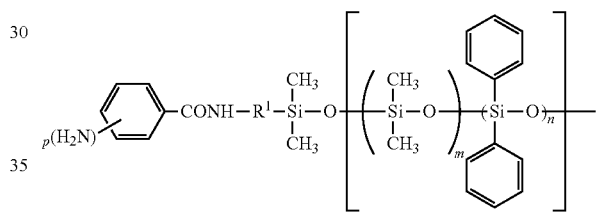

(1)

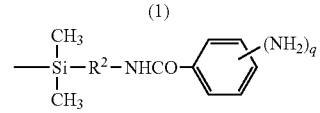

wherein $R^1$ and $R^2$ each independently represent an alkylene group which may be substituted; p denotes an integer of 0 to 3; q denotes an integer of 0 to 3; m denotes an integer of 1 to 30; and n denotes an integer of 0 to 20; provided that p and q are not 0 at the same time.

2. The method according to claim 1, wherein $R^1$ and $R^2$ are both a trimethylene group.

3. The method according to claim 1, wherein m is 1 to 20, and n is 1 to 20.

4. The method according to claim 1, wherein p and q are 1, and the amino groups at the respective ends of a molecule thereof are both connected to a para position.

* * * * *